United States Patent [19]
Kossoff

[11] 3,936,791
[45] Feb. 3, 1976

[54] LINEAR ARRAY ULTRASONIC TRANSDUCER

[75] Inventor: George Kossoff, Northbridge, Australia

[73] Assignee: The Commonwealth of Australia, Australian Capital Territory, Australia

[22] Filed: Sept. 13, 1973

[21] Appl. No.: 397,003

[52] U.S. Cl. .............. 340/1 R; 73/67.8 S; 340/8 L; 340/9
[51] Int. Cl.² ................ G01N 29/04; G01S 9/66
[58] Field of Search ............ 73/67.5 R, 67.6, 67.7, 73/67.8 R, 67.8 S, 67.9, 71.5 US; 310/8.3, 8.6, 8.7; 340/8 L, 9, 17, 15, 1 R

[56] References Cited
UNITED STATES PATENTS

| | | |
|---|---|---|
| 3,086,195 | 4/1963 | Halliday ..................... 73/67.8 S X |
| 3,166,731 | 1/1965 | Joy ............................. 73/67.8 S X |
| 3,325,781 | 6/1967 | Harris .......................... 73/67.7 X |
| 3,693,415 | 9/1972 | Whittington ................ 73/67.8 S X |

Primary Examiner—Richard C. Queisser
Assistant Examiner—John P. Beauchamp

[57] ABSTRACT

Apparatus for ultrasonic examination of objects, particularly in medical diagnostic examination, is comprised of a phased array transducer capable of focusing the beam of ultrasonic pulses in the longitudinal plane of the transducer, and focusing means to focus the dimensions of the beam normal to the longitudinal plane.

3 Claims, 11 Drawing Figures

LINEAR ARRAY ULTRASONIC TRANSDUCER

BACKGROUND OF THE INVENTION

This invention relates to the technique of ultrasonic echoscopy of objects and in particular to an extension of known techniques of ultrasonic echoscopy to provide more useful information concerning the examined objects. It is particularly, but not solely, directed to the more effective acquisition of data in medical diagnosis utilising this technique.

Ultrasonic echoscopy provides information about an examined object which may be displayed in the form of an ultrasonic echogram. Such an echogram consists of a display of acoustic impedance discontinuities or reflecting surfaces in the object. It is obtained by directing a short pulse of ultrasonic energy, typically in the 1–30 MH z frequency range, into the examined object where any acoustic impedance discontinuities in the object reflect and return some of the energy in the form of an echo. This echo is received, converted into an electric signal and displayed as an echogram on a cathode ray oscilloscope, a film, a chart or the like.

The echogram may constitute either a one dimensional or a two dimensional representation and in both cases the information is contained in the position and magnitude of the echo displayed. In a one dimensional display, the position along a base line is used to indicate the distance to the reflecting surface whilst the magnitude of the echo is displayed, for example, as a deflection of the base line or as an intensity change. In a two dimensional display, the position along a base line is used to indicate the distance to the reflecting surface as in a one dimensional display, and the direction of the base line is used to represent the direction of propagation of the acoustic energy. The two dimensional display is obtained by changing this direction of propagation of the acoustic energy and by instituting a similar but not necessarily identical movement of the base line of the display. The magnitude of the echo is displayed as for a one dimensional display; for example, as a deflection of the base line or as an intensity change.

The technique of ultrasonic echoscopy is used in medical diagnosis to obtain information about the anatomy of patients. The application of the technique is now widely investigated and is described, for example, by D. E. Robinson in Proceeding of the Institution of Radio and Electronics Engineers Australia, Vol. 31, No. 11, pages 385–392, November, 1970; "The Application of Ultrasound in Medical Diagnosis". As pointed out in this article, ultrasonic echoscopy may be used to produce displays resembling anatomical cross-sections which have proved clinically useful when the desired information concerns physical dimensions, shapes of organs or structures or the like. Ultrasonic echography has proved of particular value as a diagnostic aid in the abdomen and pregnant uterus, eye, breast, brain, lung, kidney, liver and heart, these being areas of soft tissue with little bone and air. In general, the technique is considered to complement other techniques to provide a more complete picture of the patients condition, however particularly in pregnancies, ultrasonic echoscopy may be useful in place of X-rays where the latter may not give sufficient information or may be dangerous. In medical use, a pulse of ultrasonic energy is transmitted into a patient in a known direction and echoes are received from reflecting surfaces within the body. The time delay between a transmitted pulse and the received echo depends on the distance from the transmitter to the reflecting surface and the distance information so obtained may be displayed in a suitable way for interpretation and clinical use as a one dimensional range reading or as a two dimensional cross section as previously described.

If a pulse of ultrasound is propagated into a medium, echoes will be received at various time delays and these time delays will be proportional to the distances from the transducer producing the pulse to the interfaces provided the velocity of propagation is constant. In soft tissues found in the human body the velocity of sound is reasonably constant and pulsed ultrasound provides a convenient method of measuring the depth of a particular structure from the transducer face without inconvenience to the patient. This information can be used in a number of ways.

In the simplest form of display, "A mode", the echoes are presented as deflections of the trace of an oscilloscope in which distance is represented along the time axis. This mode is useful clinically when the source of the various echoes displayed can be positively identified. It is possible to measure the distance between two echoes, or between the energising pulse and an echo, with accuracy but it may not be possible to identify the source of the echoes. It has been used to measure the size of the baby's head inside the uterus, the depth of the eye and the bladder and to locate the mid-line in the brain. Similar information may be displayed by use of the "B mode" in which the echoes are presented as a brightening or intensity modulation of the time-base trace.

If the interface of interest is moving, its position may be plotted with time ("M mode") by using the B mode presentation and allowing the time base to be swept at right angles to its direction so as to display the movements of the interface echo backwards and forwards along the time base. This is used to demonstrate the pulsatile movements of various parts of the heart and brain. If the B mode is used but the trace on the screen is made to represent the line of sight of the transducer and then the transducer is scanned around the patient and the time base line on the screen made to follow, a two-dimensional plot of impedance discontinuities is obtained. Two dimensional visualisation has been used in the pregnant uterus, abdomen, eye and breast.

Coupling from the transducer to the patient may be achieved by skin contact or by use of a water delay bath. If a water delay bath is used the distance between the transducer and the skin surface must be greater than the largest depth of penetration to be used, to avoid ambiguity due to multiple reflection. In general the skin contact scan results in greater comfort for the patient and echograms of less clarity while the water delay scan gives less patient comfort and better quality echograms.

Focusing of transducers used in ultrasonic echoscopy is known to reduce the width of the ultrasonic beams generated by the transducer and thus improve the lateral resolution. Known methods of reducing the width of an ultrasonic beam by focusing or shaping the beam include (i) focusing with a lens or a mirror in a manner similar to focusing in optics, (ii) use of a curved transducer, and (iii) use of a multi-element transducer (known as a phased array) in which the elements of the transducer are energized at progressively different times to generate the desired shape of the beam.

SUMMARY OF THE INVENTION

The present invention relates to the use of cylindrical focusing to reduce, in one plane, the width of an ultrasonic beam emitted by a phased array transducer where the dimensions of the beam normal to the focused plane are controlled by electronic means.

According to this invention, there is provided apparatus for the ultrasonic examination of an object comprising a phased array transducer capable of directing pulses of ultrasonic energy along a beam into the said object and of focusing and scanning the beam in the longitudinal plane of the transducer, and focusing means for focusing the dimensions of said beam normal to the longitudinal plane of the transducer.

The means for focusing the transducer beam in the plane normal to the longitudinal plane of the transducer may comprise a cylindrical lens or a mirror. Alternatively a curved surface transducer may be employed.

BRIEF DESCRIPTION OF THE DRAWINGS

Other objects and features of the invention will be apparent from the accompanying drawing which schematically represents an embodiment of the present invention.

In the drawings.

DESCRIPTION OF THE PREFERRED EMBODIMENTS

The direction and shape of an ultrasonic beam emitted by a phased array transducer 1 composed of a number of narrow rectangular elements $E_1, E_2, E_{n-1}, E_n$ may be set by energising the elements at progressively different times. For instance the beam may be deviated by an angle $\theta$ by energising the outer element say $E_1$ first and then progressively energising the successive elements until the other outer element $E_n$ is reached, the time interval between the energising pulses being determined by the value of the angle $\theta$ and the distance between the elements. Focusing is achieved by energising the central element first and progressively energising to the elements on either side until the outer elements are reached. A combination of the two allows simultaneous deviation and focusing of the beam. Scanning of the beam may be also obtained by energising a section of the phased array transducer, the scanning then being achieved by energising different sections of the transducer. This electronic shaping and scanning of the beam however is achieved only in the long axis plane of the phased array transducer i.e. the x-y plane, while the shape of the beam in the width plane i.e., the z-y plane is determined by the dimensions of the width of the phased array transducer.

The present invention is embodied in the use of cylindrical uni or multi curved focusing either by means of the lens 2 illustrated in the Figure, a mirror or a curved surface transducer to narrow the width of the ultrasonic beam in the z-y plane. This reduction in width is obtained independent of the beam shaping effects obtained by electronic means in the x-y plane.

Figure 1:
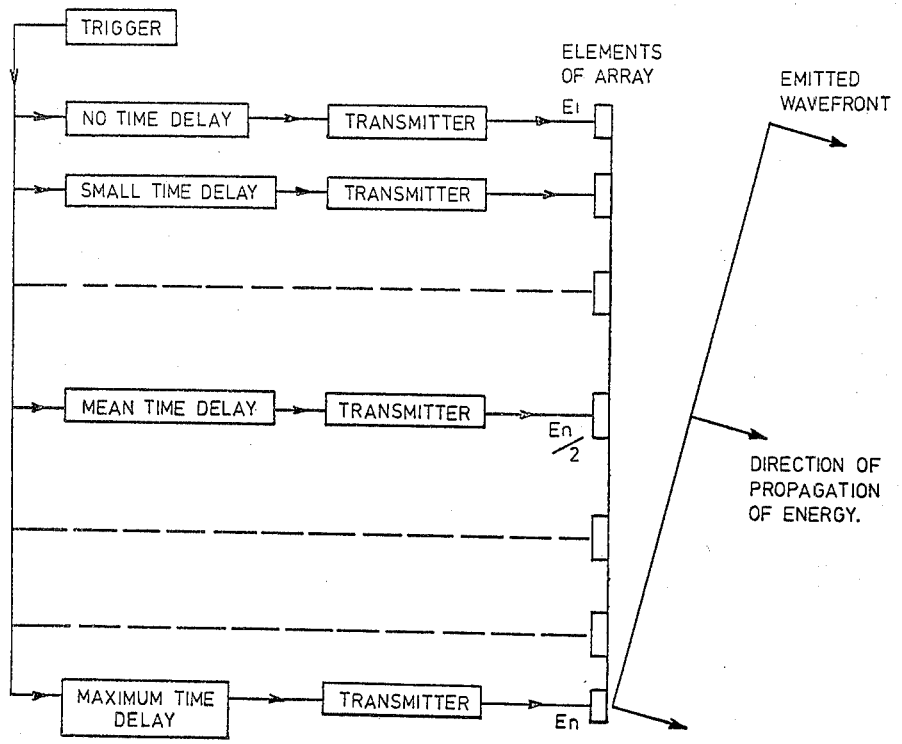
FIG. 1 depicts electronic steering of beam by use of increasing time delays in energising elements El, ... En of the array, as known in the prior art.
Figure 2:
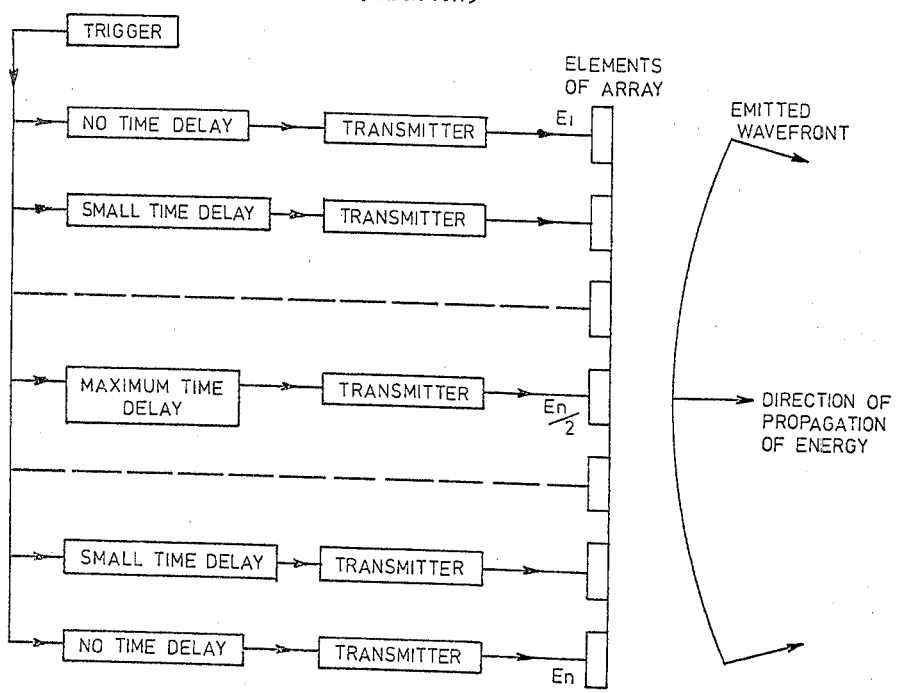
FIG. 2 depicts electronic focusing of beam by use of time delays in energising El, En; ... En/$_2$ of the array, as known in the prior art.
Figure 3:
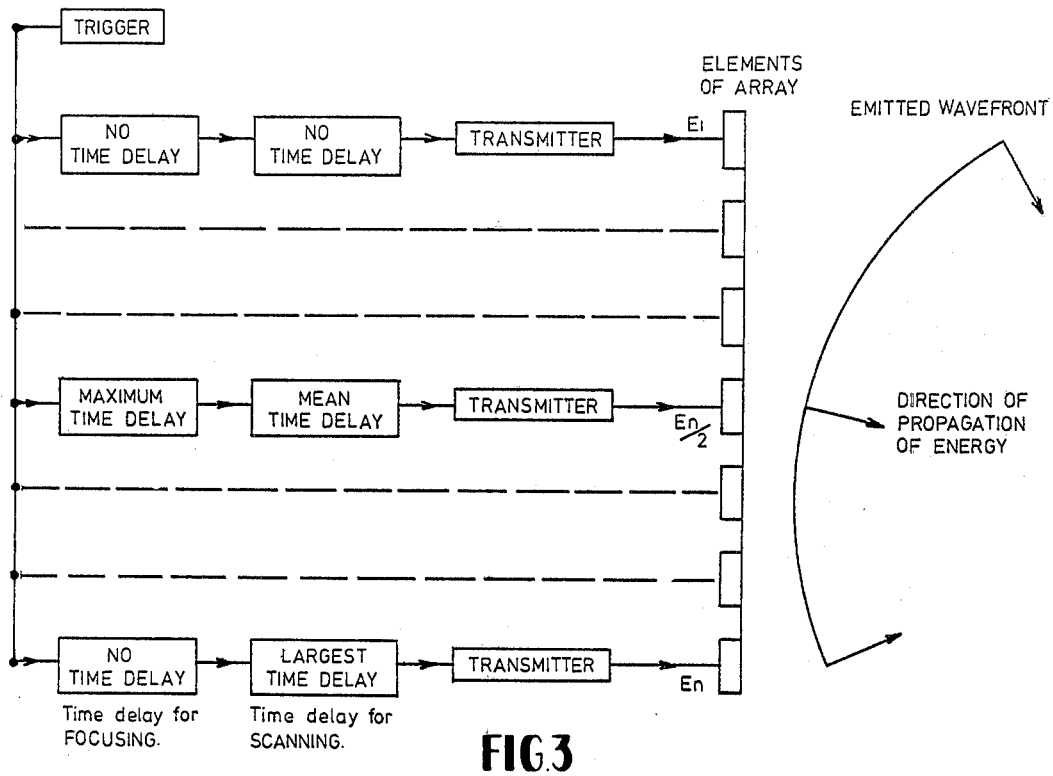
FIG. 3 depicts electronic steering and focusing of beam by combining time delays as depicted in FIGS. 1 and 2, as known in the prior art.
Figure 4:
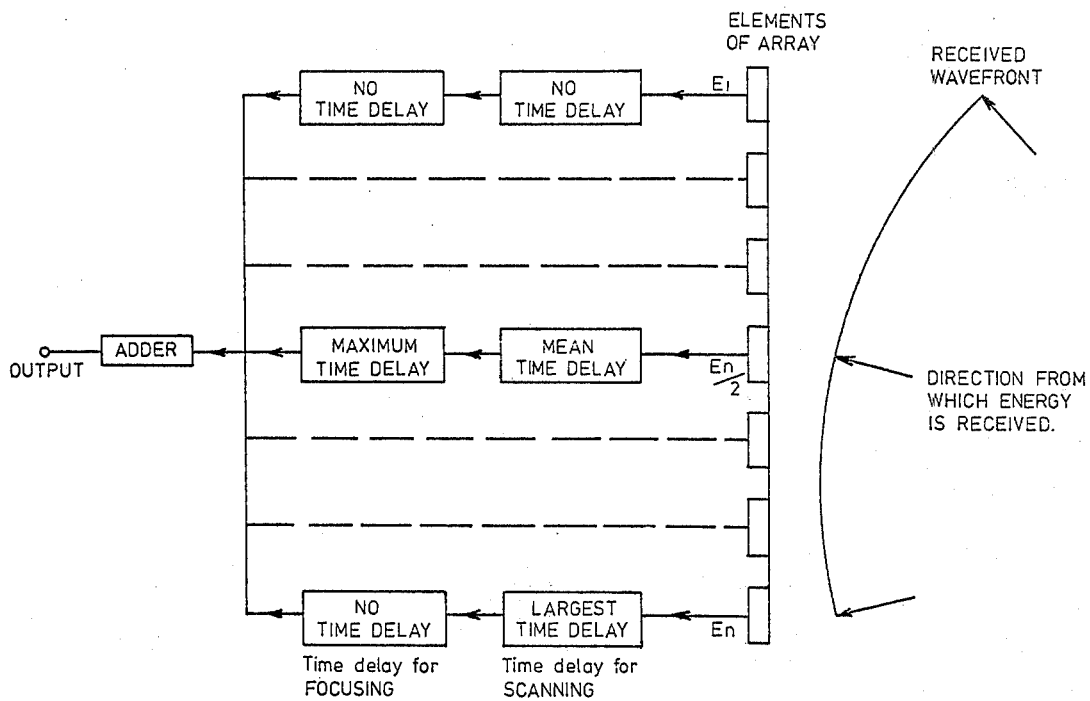
FIG. 4 depicts reception of reflected echoes in an electronically steered and focused beam, as known in the prior art.
Figure 5:
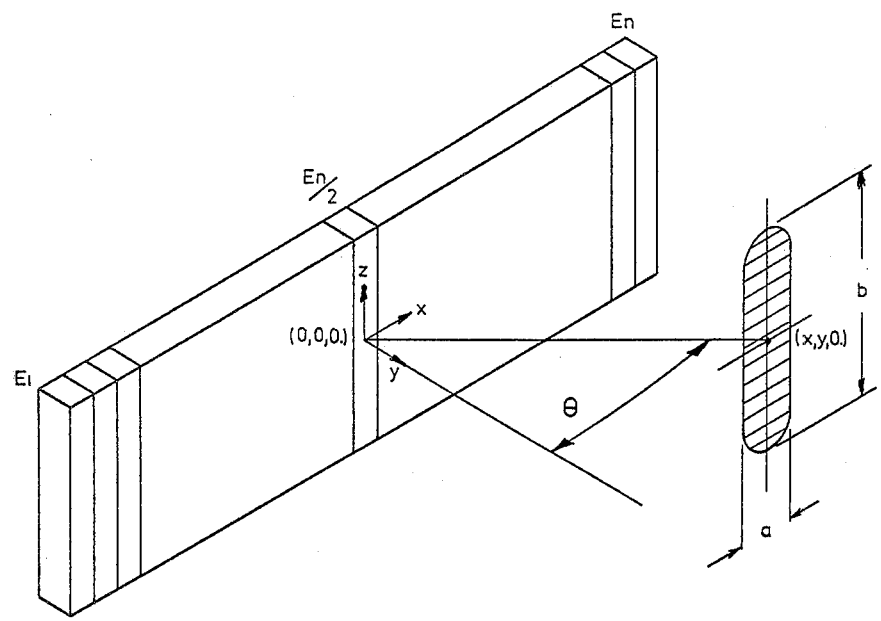
FIG. 5 illustrates the shape of an electronically steered and focused beam from linear transducer array El, .... En, as known in the prior art.
Figure 6:
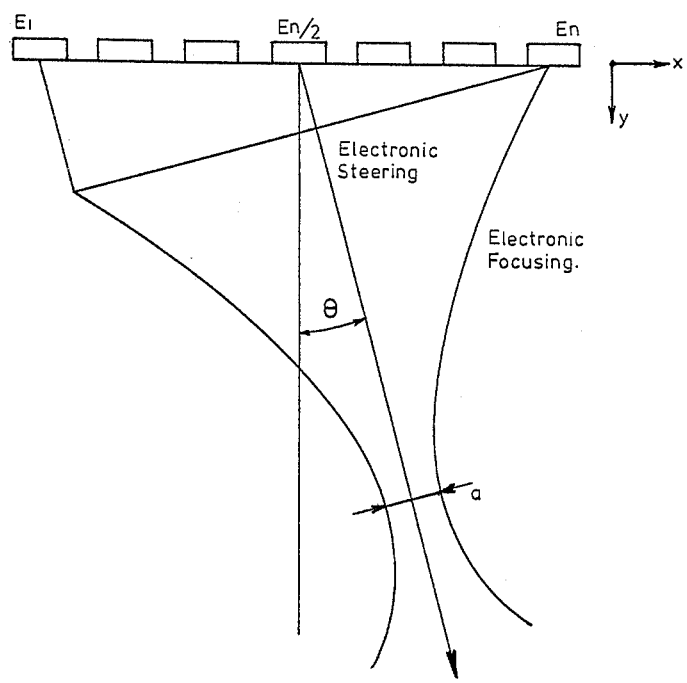
FIG. 6 illustrates effects of electronic steering and focusing of the beam in the x, y plane, as known in the prior art.
Figure 7:
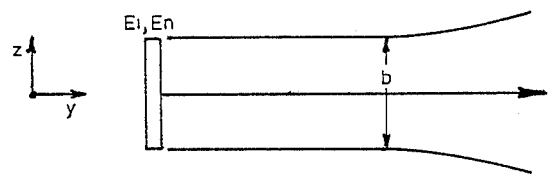
FIG. 7 illustrates that there is no focusing in the z, y plane of the beam from the linear transducer array El, ... En, as known in the prior art.
Figure 8:
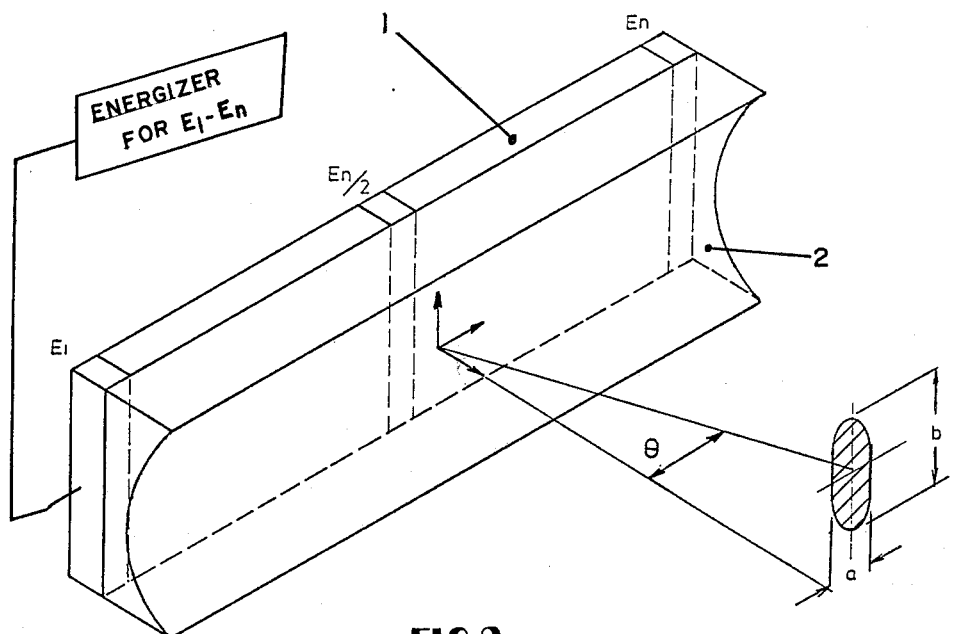
FIG. 8 illustrates the shape of an electronically steered and focused beam from linear transducer array El, ... En, focused in the x, y plane, in accordance with this invention.
Figure 9:
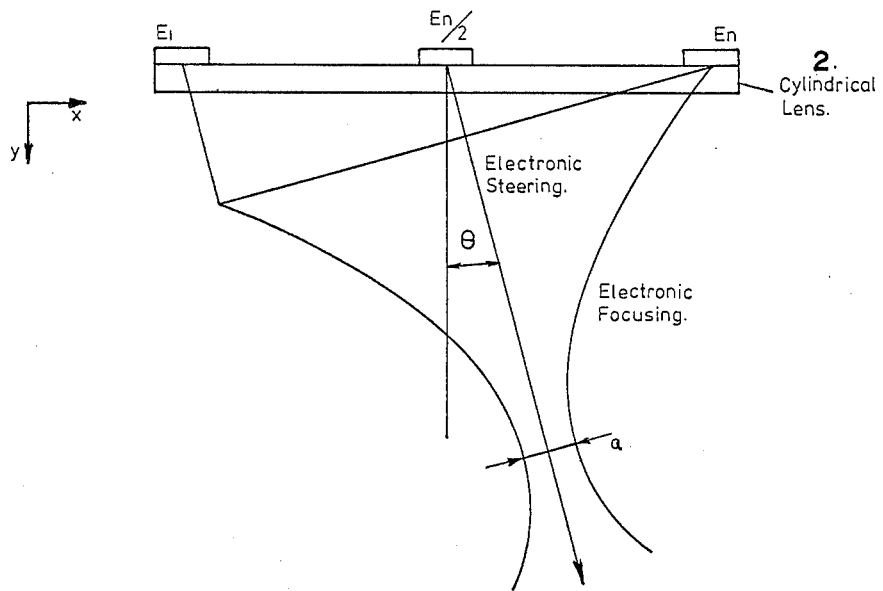
FIG. 9 illustrates that the electronic steering and focusing in the x, y plane is unchanged, in accordance with this invention.
Figure 10:
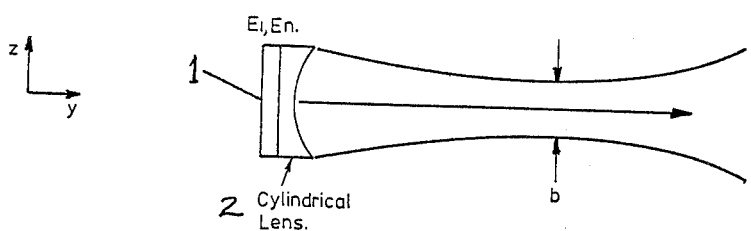
FIG. 10 illustrates the effects of focusing in the z, y plane in accordance with this invention.
Figure 11:
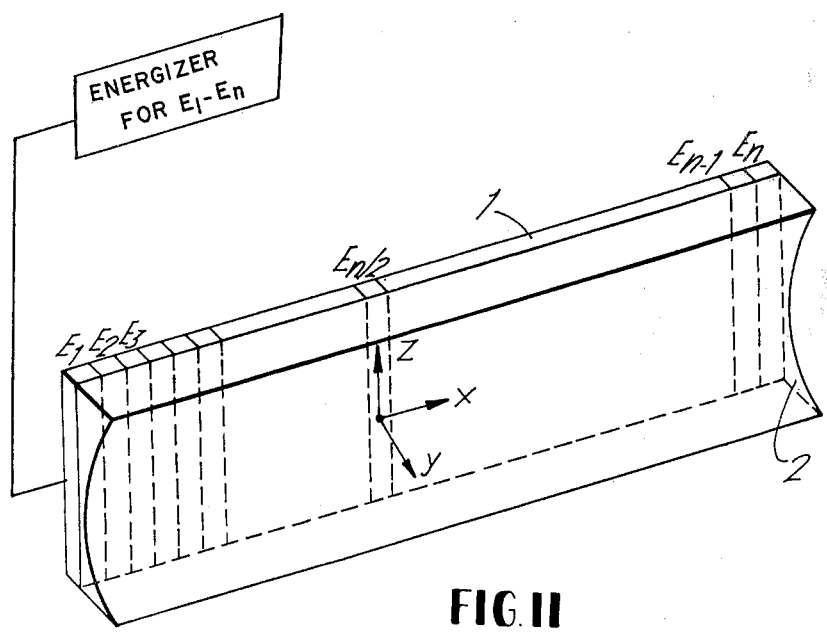
FIG. 11 illustrates the apparatus in accordance with this invention comprising a phased array transducer, energizing means for the elements of the array, and means for focusing the beam from the transducer in the z-y plane.

FIGS. 1–7 illustrates electronic steering, focusing, and reception of beams according to the prior art which is further described in U.S. Pat. No. 3,166,731 to I. L. Joy and U.S. Pat. No. 3,086,195 to W. Halliday. FIG. 1 depicts known electronic steering, and FIG. 2 depicts known electronic focusing, both achieved by utilizing appropriate time delay techniques. FIGS. 3 and 4 depict a summation of these known techniques utilizing a combination of the time delays to achieve both steering and focusing during transmission and reception.

From the foregoing description it will therefore be appreciated that the present invention provides focusing to reduce the width of an ultrasonic beam electronically focused in the dimensions normal to the focused plane. While the invention has been described with reference to an illustrative embodiment, it will generally be understood by those skilled in the art that various changes may be made and equivalents be substituted for elements thereof without departing from the true spirit and scope of the invention.

The claims defining the invention are as follows:

1. Apparatus for the ultrasonic examination of an object comprising:
   a phased array transducer comprising a plurality of transducer elements for directing pulses of ultrasonic energy along a beam into the said object;
   means for exciting the elements of the array in phased relation for focusing and scanning the beam in the longitudinal plane of the transducer; and
   focusing means for focusing the dimensions of said beam normal to the longitudinal plane of the transducer.

2. Apparatus as claimed in claim 1 characterized in that: said phased array transducer is comprised of a plurality of narrow rectangular elements, and said means for focusing and scanning the beam comprises means for energising said elements at progressively different times.

3. Apparatus as claimed in claim 1 characterized in that said focusing means comprises a cylindrical lens.

* * * * *